(12) United States Patent
Thompson et al.

(10) Patent No.: US 9,927,441 B1
(45) Date of Patent: Mar. 27, 2018

(54) COMBINATORIAL METHODS FOR APTAMER BASED PROTEOMICS

(71) Applicant: X Development LLC, Mountain View, CA (US)

(72) Inventors: Jason Thompson, Redwood City, CA (US); Jonathan Ross, Mountain View, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 15/223,062

(22) Filed: Jul. 29, 2016

(51) Int. Cl.
*C12N 15/115* (2010.01)
*G01N 33/68* (2006.01)

(52) U.S. Cl.
CPC .............................. *G01N 33/6842* (2013.01)

(58) Field of Classification Search
None
See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 7,672,786 B2 | 3/2010 | Krylov et al. |
| 8,852,893 B2 | 10/2014 | Shuber |
| 9,315,804 B2 | 4/2016 | Brown |
| 2009/0042206 A1 | 2/2009 | Schneider et al. |
| 2015/0011397 A1 | 1/2015 | Lewis et al. |
| 2015/0017662 A1 | 1/2015 | Hah et al. |
| 2016/0003809 A1 | 1/2016 | Dunaway |

FOREIGN PATENT DOCUMENTS

WO 2015054663 A2 4/2015

OTHER PUBLICATIONS

Galievsky et al (Anal. Chem. 2015, 87, 157-171).*
Gold et al.,"Aptamer-Based Multiplexed Proteomic Technology for Biomarker Discovery", PLoS One, Dec. 2010, vol. 5, Issue 12, pp. 1-17.

* cited by examiner

*Primary Examiner* — Richard A Schnizer
(74) *Attorney, Agent, or Firm* — McDonnell Boehnen Hulbert & Berghoff LLP

(57) ABSTRACT

A method for determining concentrations of target proteins in a protein sample can involve: (i) contacting the protein sample with an aptamer library to form a mixture; (ii) allowing the aptamers in the aptamer library to bind to the target proteins in the protein sample; (iii) removing the aptamers that have not been bound to a target protein in the mixture; and (iv) measuring the concentration each aptamer bound to proteins in the mixture. The concentration of a particular protein in the protein sample can be derived from the measurements of the concentrations of the aptamer or aptamers bound to that particular protein in the mixture.

19 Claims, 2 Drawing Sheets

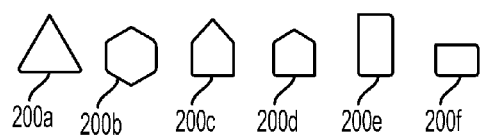
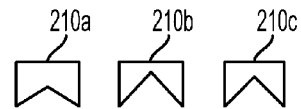
FIG. 2A
FIG. 2B
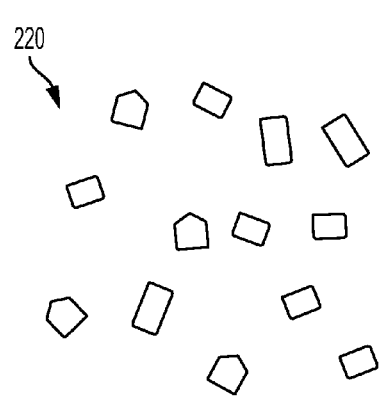
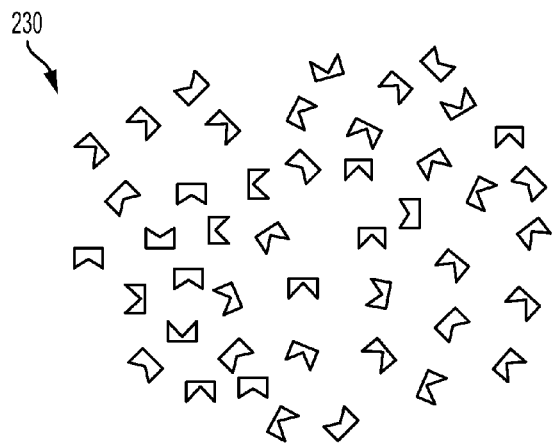
FIG. 2C
FIG. 2D
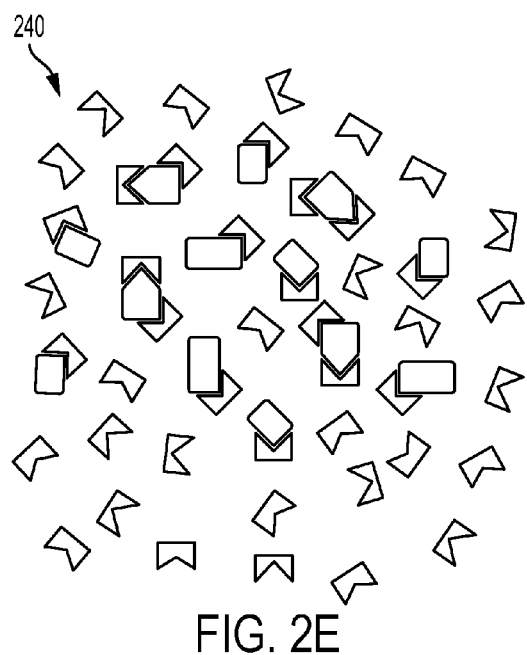
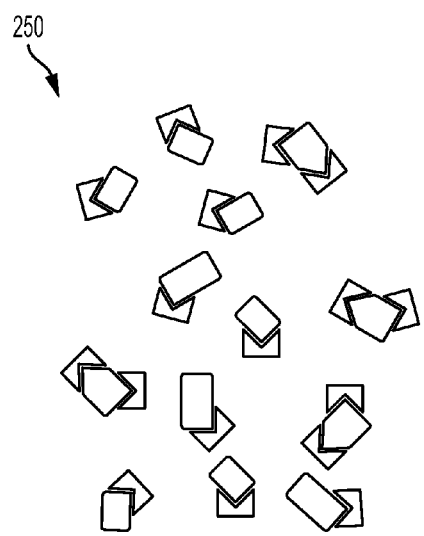
FIG. 2E
FIG. 2F

COMBINATORIAL METHODS FOR APTAMER BASED PROTEOMICS

BACKGROUND

Unless otherwise indicated herein, the materials described in this section are not prior art to the claims in this application and are not admitted to be prior art by inclusion in this section.

Proteomics seeks to understand how proteins function in their native environment with the overall intention of gaining an understanding of their biological function. One aspect of proteomics deals with the quantitative study of protein expression, which can help identify the main proteins found in a particular sample. Another aspect of proteomics deals with the qualitative and/or quantitative study of protein expression between samples that differ by certain variables, which can help identify proteins that are differentially expressed in related samples, e.g. when comparing the protein composition and abundance in pathologically altered cells contrasted with normal, healthy cells.

A challenge to the analysis of proteins from these biological samples is the complexity of the samples, which often consist of numerous proteins in varying abundances. Measuring the abundance of the various proteins in biological samples is currently a challenging, labor intensive task. High-throughput technologies have been developed for such measurements, the most commonly applied technology being mass spectrometry (MS)-based techniques such as tandem-MS technologies. However, the total throughput of these types of measurements is limited by the mass spectrometer, which is an inherently serial device.

Nucleic acid macromolecules (e.g. DNA or RNA) known as aptamers have been utilized to detect the presence of particular proteins. In these techniques, an aptamer designed to bind tightly to a specific molecular target, such as a protein, is mixed with the sample. Standard techniques are then utilized to detect the aptamer, which indicates the presence of the target protein in the sample. For example, Shuber (U.S. Pat. No. 8,852,893) describes methods of using an aptamer to detect a particular protein in a sample. Methods have also been developed for using aptamers to quantify the amount of particular proteins in a sample. For example, Gold et al. describe an aptamer-based method capable of simultaneously measuring hundreds proteins from a small sample volume (Gold L, Ayers D, Bertino J, et al. Aptamer-Based Multiplexed Proteomic Technology for Biomarker Discovery. Gelain F, ed. PLoS ONE. 2010; 5(12):e15004. doi:10.1371/journal.pone.0015004).

A common feature of these aptamer techniques is that each aptamer has been designed to bind to one particular target protein. A number of such aptamers are combined to create an aptamer library capable of detecting and/or quantifying a number of proteins. Using such techniques, a library on the order of tens of thousands of aptamers would be needed to achieve complete coverage of an entire proteome of a human cell.

SUMMARY

Implementations disclosed herein can provide improvements over conventional aptamer-based methods for qualitative and/or quantitative detection of proteins, such that quantitative analysis of numerous proteins is possible in a rapid and reliable way. In particular, methods are provided for determining concentrations of target proteins in a protein sample using aptamers that can bind to one or more of the target proteins in the sample. Using information about the forward ($k_f$) and reverse ($k_r$) reaction rates for each aptamer-protein binding pair and the measurements of the amounts of the various aptamers bound to proteins in the protein sample, the concentration of the target proteins in the samples is determined according to the methods of the present disclosure. Methods described herein provide for determination of the concentration of a target protein in a complex biological sample, even if the target protein is present in a small amount. Methods described herein may allow for the determination of the concentration of a number of target proteins in a single assay using fewer aptamers than would be needed to quantify the same number of proteins using conventional aptamer-based methods.

The disclosed implementations provide a method for determination of the concentration of a target protein in a sample that includes: (i) bringing into contact together to form an aptamer/protein mixture: (A) an aptamer library, wherein the library comprises a plurality of aptamers each having a property of binding to one or more of the target proteins in the sample and the forward ($k_f$) and reverse ($k_r$) reaction rates for each aptamer-protein binding pair is known, and (B) the protein sample, comprising the target proteins in unknown concentrations; (ii) allowing the aptamers in the aptamer library to bind to the target proteins in the protein sample; (iii) removing the aptamers that have not been bound to a target protein in the aptamer/protein mixture; and (iv) measuring the concentration of each aptamer bound to proteins in the aptamer/protein mixture, wherein the concentration of a particular protein in the protein sample can be derived from the measurements of the concentrations of the one or more aptamers from the aptamer library bound to the particular protein in the aptamer/protein mixture.

These as well as other aspects, advantages, and alternatives, will become apparent to those of ordinary skill in the art by reading the following detailed description.

BRIEF DESCRIPTION OF THE DRAWINGS

FIG. 2A schematically illustrates example proteins that may be present in a protein sample, in which different shapes indicate different proteins.

FIG. 2B schematically illustrates three different aptamers, in which different shapes indicate different aptamers.

FIG. 2C schematically illustrates an example protein sample that includes example proteins illustrated in FIG. 2B, before interaction with aptamers.

FIG. 2D schematically illustrates an example aptamer library comprising the example aptamers illustrated in FIG. 2B, before interaction with a protein sample.

FIG. 2E schematically illustrates an example aptamer/protein mixture with example aptamer-protein binding pairs, resulting from interaction of the example protein sample of FIG. 2C with the example aptamer library illustrated in FIG. 2D.

FIG. 2F schematically illustrates example aptamer-protein binding pairs that remain after removal of aptamers that have not bound to a protein in the aptamer/protein mixture illustrated in FIG. 2E.

DETAILED DESCRIPTION

Figure 1:
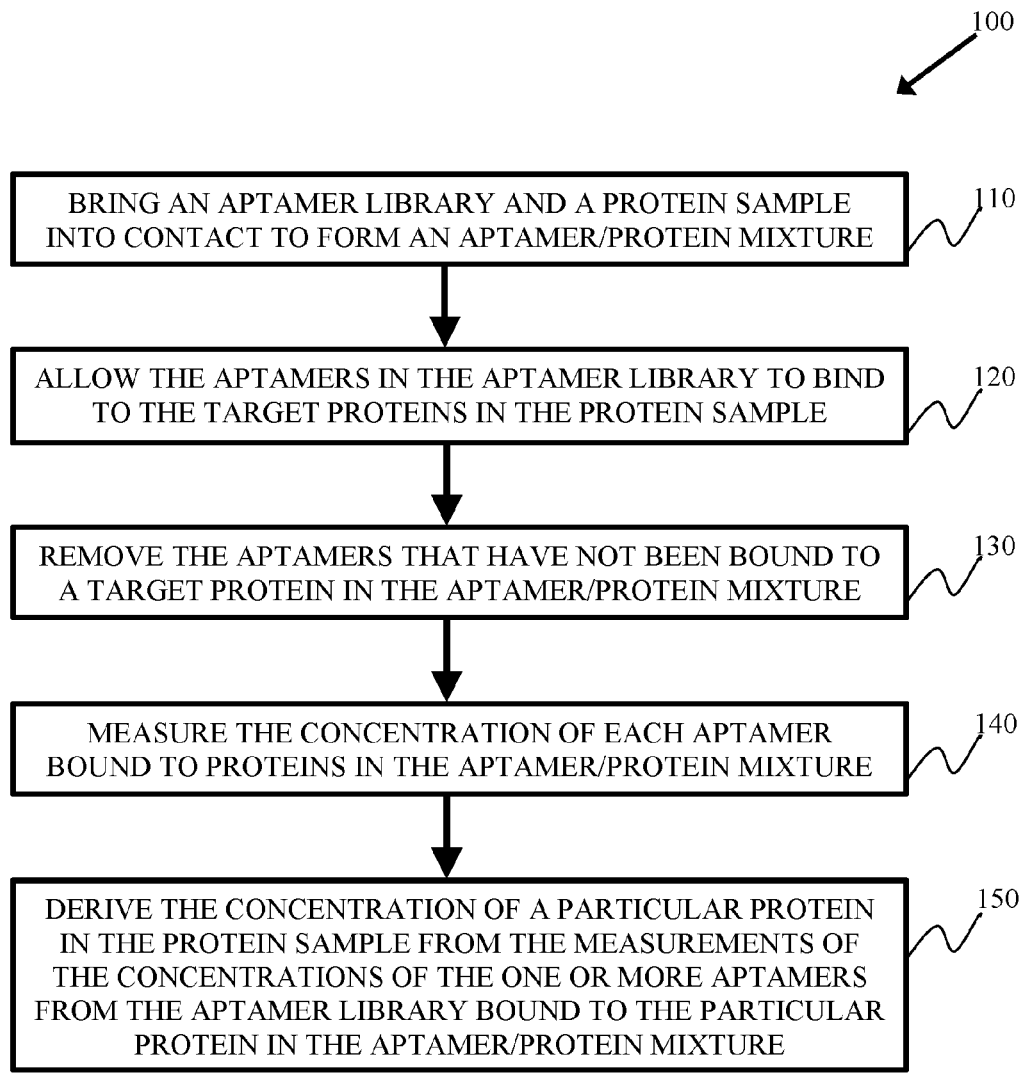
FIG. 1 is a flowchart of an example method.

In the following detailed description, reference is made to the accompanying figures, which form a part hereof. The illustrative implementations described in the detailed description, figures, and claims are not meant to be limiting. Other implementations may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

The present disclosure involves the use combinatorial approaches to aptamer-based recognition assays for the measurement of a protein's abundance in a protein mixture, such as a complex biological sample, that takes advantage of the aptamer-protein interaction. Methods of the present disclosure allow for the determination of the concentration of a target protein in the protein sample, even if the target protein in present in a small amount. In certain implementations, methods of the present disclosure are accomplished by adding an aptamer to a protein sample, which allows the aptamer to bind a target protein in the sample to form a bound aptamer-protein pair. Generally, an aptamer is a nucleic acid macromolecule (e.g. DNA or RNA) that binds tightly to a specific molecular target, such as a protein. However, the aptamers used in the methods of the present disclosure do not need to be optimized to bind to a single target protein. Rather, the aptamers used in the present disclosure may have a specific binding affinity for a single target molecule, or may bind to more than one target molecule. Thus, as used herein, the term "aptamer" refers to a nucleic acid that has a binding affinity for one or more target molecules, such as proteins.

Typical aptamer-based recognition assays rely on the specificity of the aptamer for a single target protein. For such a protein-specific aptamer, the reaction between the aptamer (A) and the target protein (P) is described by equation 1:

$$[A]+[P] \leftrightarrow [AP] \tag{1}$$

where AP is the aptamer-protein pair and square parentheses are used to denote concentration. The forward and reverse reaction rates of the reaction are denoted as $k_f$ and $k_r$, respectively.

The kinetics of this reaction are described by the ordinary differential equation shown in equation 2:

$$d[AP]/dt=[A][P]k_f-[AP]k_r \tag{2}$$

where t is time.

One potential objective of the disclosed aptamer measurement methods is to determine the initial concentration of the target protein, [P], for each of the target proteins in a protein sample.

Using a protein-specific aptamer, the target protein concentration can be measured by measuring the amount of aptamer bound to the protein ([AP]). This method for quantitation of protein concentration involves (a) creating an aptamer/protein mixture by incubating the protein sample containing the protein of interest (P) with a large molar excess of aptamer (A) for a period of time that allows the aptamer-target protein binding reaction to reach equilibrium (d[AP]/dt=0); (b) washing the mixture to remove any unbound aptamer (A) over a time scale faster than the reverse reaction rate ($k_r$); and (c) measuring the concentration of the bound aptamer ([AP]). In the case of an aptamer library, the incubation time would be a length of time that allows each of the aptamer-target protein binding reactions to reach equilibrium. With information about the forward ($k_f$) and reverse ($k_r$) reaction rates for each of the aptamer-protein binding pairs, an appropriate incubation time can be determined.

Under these conditions, it can assumed that there is no free aptamer ([A]=0) or free protein ([P]=0) at the time of measurement. Thus, the measurement of the bound aptamer (m) obtained by measuring [AP] is measurement of the initial concentration of the target protein of interest (m=[AP]=[P]).

When the aptamer library consists of aptamers that each bind to a single target protein of interest and does not cross-react with any other proteins, it can be assumed that the measurements of the concentrations of the bound aptamers ([AP]) are independent and, thus, the above-described measurement method can be carried out for many proteins in parallel without complication. Numerous proteins can be detected and/or quantitated simultaneously by utilizing an aptamer library containing tens, hundreds, or thousands of protein-specific aptamers.

However, if completely independent aptamers (i.e., each aptamer is specific to a single target protein) cannot be or are not prepared, the measurement of the initial target protein concentration is more complicated. This is illustrated for the simple case of two aptamers, $A_1$ and $A_2$, each of which binds to the same two proteins, $P_1$ and $P_2$, and no others. The reactions between these two aptamers and two proteins can be described by the four reactions shown in equations 3-6:

$$[A_1]+[P_1] \leftrightarrow [A_1P_1] \tag{3}$$

$$[A_1]+[P_2] \leftrightarrow [A_1P_2] \tag{4}$$

$$[A_2]+[P_1] \leftrightarrow [A_2P_1] \tag{5}$$

$$[A_2]+[P_2] \leftrightarrow [A_2P_2] \tag{6}$$

Each of the above reactions has a corresponding forward ($k_f$) and reverse ($k_r$) reaction rate. The kinetics of the reactions are described by the set of four coupled ordinary differential equations shown in equations 7-10:

$$d[A_1P_1]/dt=[A_1][P_1]k_{f11}-[A_1P_1]k_{r11} \tag{7}$$

$$d[A_1P_2]/dt=[A_1][P_2]k_{f12}-[A_1P_2]k_{r12} \tag{8}$$

$$d[A_2P_1]/dt=[A_2][P_1]k_{f21}-[A_2P_1]k_{r21} \tag{9}$$

$$d[A_2P_2]/dt=[A_2][P_2]k_{f22}-[A_2P_2]k_{r22} \tag{10}$$

Using these exemplary aptamers, $A_1$ and $A_2$, in the measurement method described for the target protein-specific aptamer case (incubate with a molar excess of aptamers, wait for each of the aptamer-target protein binding reactions to reach equilibrium, wash, and measure each bound aptamer), a measurement of bound aptamer (e.g., $[A_1P_1]$) does not serve as measurement of the initial concentration of any one protein. Rather, the measurement for each bound aptamer is the result of the measurements from a mixture aptamer-protein pairs. In the above example, the measurements for aptamer 1 ($m_1$) and for aptamer 2 ($m_2$) are the results of the measurements of the bound aptamer-protein pairs given in equations 11-12:

$$m_1=[A_1P_1]+[A_1P_2] \tag{11}$$

$$m_2=[A_2P_1]+[A_2P_2] \tag{12}$$

whereas the initial protein concentrations for protein 1 ($[P_1]$) and protein 2 ($[P_2]$) are the results of the bound aptamer-protein pairs given in equations 13-14:

$$[P_1]=[A_1P_1]+[A_2P_1] \tag{13}$$

$$[P_2]=[A_1P_2]+[A_2P_2] \tag{14}$$

Thus, determining the initial protein concentration ([P]) in situations where an aptamer binds to more than one protein in a protein sample may involve obtaining and using additional information.

The present disclosure describes methods for determining the abundance of proteins in a protein mixture, such as a biological sample, using a mixture of aptamers (an aptamer library) that contains one or more aptamers that do not uniquely bind a single target protein. Additional information about the interaction of the individual aptamers in the aptamer library with their target protein(s) is used to determine the initial concentration of the component proteins in a protein mixture.

FIG. 1 illustrates elements of such a method 100. The method 100 includes bringing into contact together to form an aptamer/protein mixture: (A) an aptamer library and (B) a protein sample (110). The aptamer library includes a plurality of aptamers each having a property of binding to one or more of the target proteins in the sample, and the forward ($k_f$) and reverse ($k_r$) reaction rates for each aptamer-protein binding pair is known. The protein sample includes target proteins in unknown concentrations.

The method 100 also includes allowing the aptamers in the aptamer library to bind to the target proteins in the protein sample (120), removing the aptamers that have not been bound to a target protein in the aptamer/protein mixture (130), and measuring the concentration of each aptamer bound to proteins in the aptamer/protein mixture (140).

The method 100 further includes deriving the concentration of a particular protein in the protein sample from the measurements of the concentrations of the one or more aptamers from the aptamer library bound to the particular protein in the aptamer/protein mixture (150).

In one implementation, the additional information used to determine the initial concentration of the particular target proteins of interest includes the forward ($k_f$) and reverse ($k_r$) reaction rates for each bound aptamer-protein pair. In this implementation, the reaction rates, $k_{f,ij}$ and $k_{r,ij}$ (where i denotes the aptamer and j denotes the protein), are measured for each aptamer-protein pair. The forward ($k_f$) and reverse ($k_r$) reaction rates for each bound aptamer-protein pair can be determined using any method known in the art.

In this implementation, the same measurement method can be used as described above: incubate the protein mixture with a molar excess of aptamer, wait for each of the aptamer-protein binding reactions to reach equilibrium, wash, and measure (m) the concentration of each bound aptamer ([AP]). In this implementation, the incubation step is of sufficient length to allow all of the aptamer-protein binding reactions to reach equilibrium before the bound aptamer concentrations ([AP]) are measured. With information about the forward ($k_f$) and reverse ($k_r$) reaction rates for each aptamer-protein binding reaction, an appropriate incubation time can be determined. The measurements of the concentrations of the bound aptamers ([AP]) can be made using any method known in the art that allows quantitation of the individual bound aptamers.

With information about the forward ($k_f$) and reverse ($k_r$) reaction rates for the aptamer-protein binding reaction for each aptamer-protein pair, a complete set of linear equations can be built to deconvolve the initial protein concentrations ([P]) from the measurements (m) for the various bound aptamers ([AP]).

FIGS. 2A-2F illustrate an example process of using aptamers from an aptamer library to bind with proteins in a protein sample, such that the concentrations of a particular protein in the protein sample can be determined. In FIGS. 2A-2F, different shapes represent different proteins and different aptamers. FIG. 2A schematically illustrates six example proteins (200a, 200b, 200c, 200d, 200e, 200f) that may be present in a protein sample. FIG. 2B schematically illustrates three different aptamers (210a, 210b, 210c). The notched shapes of the aptamers (210a, 210b, 210c) shown in FIG. 2B represent the ability of the aptamers to bind with proteins. FIG. 2C schematically illustrates an example protein sample (220) that includes some of the example proteins illustrated in FIG. 2A, before interaction with aptamers. FIG. 2D schematically illustrates an example aptamer library (230) comprising the example aptamers shown in FIG. 2B, before interaction with a protein sample. FIG. 2E schematically illustrates an example aptamer/protein mixture (240) with example aptamer-protein binding pairs, resulting from interaction of the example protein sample (220) shown in FIG. 2C with the example aptamers in the example aptamer library (230) shown in FIG. 2D. FIG. 2F schematically illustrates example aptamer-protein binding pairs (250) that remain after removal of aptamers that have not bound to a protein in the aptamer/protein mixture (240) shown in FIG. 2E. The concentration of each aptamer in the aptamer-protein binding pairs (250) is measured, and these measurements are then used to determine the concentration of a particular protein in the protein sample (220).

The methods described herein can be used with aptamer libraries of any size. Preferably, the aptamer library contains 100 or more aptamers. More preferably, the aptamer library contains 1,000 or more aptamers. The library can comprise aptamers that are specific for a single target protein, aptamers that bind to more than one target protein, and mixtures thereof. In some implementations, the aptamer library may predominantly or exclusively comprises aptamers that do not uniquely bind a single target protein.

For aptamers in the aptamer library that have been optimized to each bind to a single target protein, the measurement (m) of the bound aptamer ([AP]) indicates the quantity of the initial concentration of the target protein. In circumstances where the aptamer library contains one or more aptamers that each can bind to more than one target protein, the initial concentration of the target proteins that bind to multiple aptamers can be determined by solving the linear equations using the bound aptamer measurements ([AP]), the initial aptamer concentrations for each of the aptamers in the aptamer library ([A]), and the information about the forward ($k_f$) and reverse ($k_r$) reaction rates for each aptamer-protein binding reaction. A linear solver may then be used to solve the set of linear equations in order to determine the initial protein concentration ([P]) for those proteins that bind to more than one aptamer in the aptamer library.

The incubation time of the aptamers and the protein sample may be of a sufficient length to allow each of the aptamer-protein binding reactions to reach equilibrium. However, in some instances, it may not be practical or desirable to wait until one or more of the aptamer-protein binding reactions have reached equilibrium before measuring the bound aptamer concentration ([AP]). For example, some aptamers may have slow forward reaction rates ($k_f$) for the binding reaction with one or more target proteins in the protein sample as compared to other aptamers in the aptamer library, such that it may be impractical or undesirable to wait for that aptamer-target protein binding reaction to reach equilibrium. Thus, in another implementation, the measurements (m) of the bound aptamer concentrations ([AP]) are made before one or more of the binding reactions in the aptamer-protein mixture have reached equilibrium. In this implementation, the additional information used to determine the initial protein concentration is two-fold. First, the forward ($k_f$) and reverse ($k_r$) reaction rates are determined for each aptamer-protein pair. Second, additional information is gathered from measurements of the concentrations of the bound aptamers at a series of time points before the aptamer-protein reaction has reached equilibrium for one or more of the aptamer-protein pairs.

For this implementation, the previously-described measurement protocol of incubating the protein sample with a molar excess of aptamer, waiting for all of the aptamer-protein binding reactions to reach equilibrium, washing, and measuring the concentration of each bound aptamer is modified. Rather than waiting for all of the aptamer-protein binding reactions to reach equilibrium, a series of aptamer-protein mixtures are created, each of which is allowed to react for a different length of time, thereby generating a time-series of aptamer-protein binding reactions that can be used for the subsequent washing and measuring steps. The series of aptamer-protein mixtures may be created by removing samples from a mixture of the aptamer library and the protein sample at different time points for (a) subsequent washing to remove any unbound aptamers and (b) measurements of the concentration of the bound aptamers ([AP]) at each of the different time points. Alternatively, identical mixtures of the aptamer library and the protein sample are prepared in parallel and the different mixtures are then selected for washing and measuring of the concentration of the bound aptamers at different time points. The measurements of the concentrations of the bound aptamers ([AP]) can be made using any method known in the art that allows quantitation of the individual bound aptamers.

With this time series data of bound aptamer concentrations ([AP]), the information about the forward ($k_f$) and reverse ($k_r$) reaction rates for each aptamer-protein pair, the starting aptamer concentration ([A]) for each of the aptamers in the aptamer library, and the set of equations describing the kinetics of the reaction between each of the target proteins and its cognate aptamer(s), a non-linear regression algorithm can be used to fit the bound aptamer concentration data from the time series to a predicted time series of the bound aptamer concentration ([$A_iP_j$](t)) to solve for the initial protein concentration of each of the proteins in the protein sample. If an analytical solution exists, it can be used in the non-linear regression algorithm to solve for the initial protein concentrations. If an analytical solution does not exist, a numerical ordinary differential (ODE) solver can be used to solve for the initial protein concentrations.

In some implementations, the aptamer-protein reactions can be manipulated to improve the aptamer-based measurements used to determine the initial protein concentration. In one implementation, the protein sample is manipulated prior to the introduction of the aptamer to separate the proteins in the sample to improve the aptamer-based measurements. For example, the highest abundance proteins may be partially or wholly removed from the sample before introduction of the aptamer, which can improve detection of proteins that are present in the protein sample in lower abundances. This can be accomplished by any one of numerous methods known in the art including, for example, by immunoprecipitation with antibodies specific for the highest abundance protein(s). Alternatively, proteins are not removed from the sample, but rather the proteins are separated and analyzed in subsets. For example, the sample can be separated by size, abundance, or any other desirable grouping.

In another implementation, particular target proteins are removed from the protein sample before the addition of the aptamer library, such as those target proteins that have faster or slower reaction kinetics with their cognate aptamer(s) as compared to other target proteins in the protein sample. Methods for such separations include, for example, chromatographic and electrophoretic separation techniques, or by using target protein-specific agents, such as antibodies, to selectively separate proteins from the protein sample prior to initiation of the quantitation methods described herein.

In yet another implementation, the aptamer-based measurements are improved by varying the ratios of the aptamers used in the aptamer library. For example, an aptamer with a fast forward reaction rate ($k_f$) for a particular target protein may be included at a low concentration in the aptamer library.

In still another implementation, both the protein sample and the aptamer library are manipulated prior to the reaction of the aptamers with the protein sample. In these implementations, the modifications to the protein sample and/or the aptamer library are accounted for when solving for the initial protein concentrations.

Aptamer libraries that have broad coverage for the particular set of proteins to be assayed do not necessarily contain aptamers that are specific to only one protein. Instead, each individual aptamer may have high sensitivity for proteins in the set, but may have relatively low specificity for any particular protein.

The implementations described herein can be used for the measurement of a large number of proteins with a relatively small number of such non-specific aptamers. The aptamers used in the aptamer libraries depend upon the target protein to be detected. Preferably, the aptamers have overlapping specificities for the proteins that cover an entire proteome.

Aptamers for the target proteins may be discovered by any method known in the art. The aptamers can be selected by screening against similar proteins, or conserved peptide regions in the proteome using an in vitro selection process referred to as SELEX (Systematic Evolution of Ligands by Exponential enrichment). See, for example, Gold et al. (U.S. Pat. Nos. 5,270,163 and 5,475,096). SELEX is an iterative process used to identify an aptamer to a chosen molecular target, such as a protein, from a large pool of nucleic acids. The process generally relies on standard molecular biological techniques, using multiple rounds of selection, partitioning, and amplification of aptamers to resolve the aptamers with the highest affinity for a target molecule. There have been numerous improvements to the basic SELEX method. See, for example, Brown (U.S. Pat. No. 9,315,804). SELEX, any of the improvements to SELEX, or any other methods known in the art for generating aptamers with specificity or affinity for one or more proteins may be used to discover aptamers for use in the methods described herein. An aptamer selection process that is not optimized for high sensitivity and specificity for a single protein can be sufficient when the implementations described herein are employed.

In the methods described herein, aptamers are introduced to the protein sample to bind to one or more of the target proteins. Certain of the aptamers bind the target protein(s) of interest in the sample to form aptamer-protein pairs. The unbound aptamers are then separated and/or removed from sample using any method known in the art. See, for example, Schneider et al., U.S. Patent Application Publication Number 2009/0042206.

The forward ($k_f$) and reverse ($k_r$) reaction rates for each aptamer-protein binding can be determined using any method known in the art, such as surface plasmon resonance, gel- or chromatographic-based methods, or spectroscopic methods.

The measurements of the concentration of an aptamer, including the bound aptamers, can be accomplished using any method known in the art. Among the methods that can be used are high-throughput nucleotide sequencing methods, quantitative real time PCR, or detectable labels, such as fluorescence or other optically-detectable labels. For example, Brown (U.S. Pat. No. 9,315,804) describes a number of sequencing, PCR, and optical detection methods, including fluorescence detection methods, that can be used or adapted to measure the concentration of bound aptamers ([AP]).

While various aspects and implementations have been disclosed herein, other aspects and implementations will be apparent to those skilled in the art. The various aspects and implementations disclosed herein are included for purposes of illustration and are not intended to be limiting, with the true scope and spirit being indicated by the following claims. Other implementations may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A method for determining concentrations of target proteins in a protein sample, comprising: (i) bringing into contact together to form an aptamer/protein mixture: (A) an aptamer library, wherein the library comprises a plurality of aptamers each having a property of binding to one or more of the target proteins in the sample and the forward ($k_f$) and reverse ($k_r$) reaction rates for each aptamer-protein binding pair is known, wherein at least one aptamer of the plurality of aptamers has a property of binding to two or more of the target proteins in the sample, and (B) the protein sample, comprising the target proteins in unknown concentrations; (ii) allowing the aptamers in the aptamer library to bind to the target proteins in the protein sample; (iii) removing the aptamers that have not been bound to a target protein in the aptamer/protein mixture; (iv) measuring the concentration of each aptamer bound to proteins in the aptamer/protein mixture; and (v) determining a concentration of a protein in the protein sample based on the measurements of the concentrations of two or more of the aptamers from the aptamer library bound to proteins in the aptamer/protein mixture.

2. The method according to claim 1, wherein in the aptamer/protein mixture, the aptamers are contained in an excess amount relative to the target proteins in the protein sample.

3. The method of claim 1, wherein at least one aptamer of the plurality of aptamers has a property of binding specifically to only one of the target proteins in the sample.

4. The method of claim 3, wherein the measurement of the concentration of one or more of the aptamers provides a direct measurement of the concentration of a particular protein in the protein sample.

5. The method of claim 1, wherein the measurement of the concentration of an aptamer provides an indirect measurement of the concentration of a particular protein in the protein sample.

6. The method of claim 1, further comprising: allowing the binding between each of the aptamers and target proteins in the aptamer/protein mixture to reach equilibrium before step (iii).

7. The method of claim 6, further comprising determining the concentration of a second target protein in the protein sample based on (i) the measurement of the concentration of each aptamer bound to proteins in the aptamer/protein mixture, (ii) the concentration of each aptamer in the aptamer library, and (iii) the forward ($k_f$) and reverse ($k_r$) reaction rates for each aptamer-protein pair.

8. The method of claim 7, wherein the concentration of each target protein in the protein sample is determined using a linear solver.

9. The method of claim 1, wherein step (iv) comprises creating a time series of measurements of the aptamer concentrations.

10. The method of claim 9, wherein samples are removed from the aptamer/protein mixture at a series of time points before the binding between the aptamers and target proteins in the aptamer/protein mixture has reached equilibrium, and those samples are immediately moved to step (iii) while the aptamers in the remainder of the aptamer/protein mixture are allowed to continue to bind to the target proteins, creating the time series of measurements of the aptamer concentrations in step (iv).

11. The method of claim 9, further comprising preparing a series of identical aptamer/protein mixtures in step (i); allowing the binding of step (ii) to occur for different lengths of time for each of the mixtures, wherein the lengths of time are shorter than the time it takes for the binding between one or more of the aptamers and one or more of the target proteins in the aptamer/protein mixture to reach equilibrium; and taking each mixture to steps (iii) and (iv) at the conclusion of the designated length of time for that mixture, thereby creating the time series of measurements of the aptamer concentrations in step (iv).

12. The method of claim 9, wherein the concentration of each target protein in the protein sample is determined using a non-linear regression algorithm to fit the time series measurements to a predicted time series of the bound aptamer concentration based on (i) the time series measurements of the concentration of each aptamer bound to proteins in the aptamer/protein mixture, (ii) the concentration of each aptamer in the aptamer library, and (iii) the forward ($k_f$) and reverse ($k_r$) reaction rates for each aptamer-protein pair.

13. The method of claim 12, wherein a numerical ordinary differential equation (ODE) solver is used to determine the protein concentrations.

14. The method of claim 1, further comprising: separating the proteins in the protein sample prior to step (i) to remove some proteins from the protein sample.

15. The method of claim 14, wherein the proteins removed are those of highest concentration.

16. The method of claim 14, wherein the proteins removed are those with the fastest forward reaction rates ($k_f$).

17. The method of claim 14, wherein the proteins removed are those with the slowest forward reaction rates ($k_f$).

18. The method of claim 1, further comprising: separating the protein sample into subsets prior to step (i) and separately determining the concentrations of target proteins in each of the subsets of the protein sample.

19. The method of claim 1, wherein the amount of one or more of the aptamers in the aptamer library is adjusted in comparison to the other aptamers in the library to improve the determination of the protein concentration of one or more of the target proteins in the protein sample.

* * * * *